(12) United States Patent
O'Lenick, Jr.

(10) Patent No.: US 6,313,329 B1
(45) Date of Patent: Nov. 6, 2001

(54) SILICONE FUNCTIONALIZED EUGENOL ESTERS

(76) Inventor: Anthony J. O'Lenick, Jr., 2170 Luke Edwards Rd., Dacula, GA (US) 30019

( * ) Notice: Subject to any disclaimer, the term of this patent is extended or adjusted under 35 U.S.C. 154(b) by 0 days.

(21) Appl. No.: 09/873,048

(22) Filed: Jun. 4, 2001

(51) Int. Cl.$^7$ .................................. C07F 7/08; C07F 7/18
(52) U.S. Cl. ........................... 554/77; 556/437; 556/438; 556/439; 514/63; 424/70.8; 424/70.12; 424/78.02; 424/78.03
(58) Field of Search ................................ 554/77; 556/439, 556/437, 438; 514/63; 424/70.12, 70.8, 78.02, 78.03

(56) References Cited

U.S. PATENT DOCUMENTS

| 5,136,063 | * | 8/1992 | O'Lenick, Jr. ........................ 554/77 |
| 5,296,625 | * | 3/1994 | O'Lenick, Jr. et al. ............. 556/437 |
| 6,114,561 | | 9/2000 | O'Lenick, Jr. . |

* cited by examiner

*Primary Examiner*—Paul F. Shaver

(57) ABSTRACT

This invention relates to composition of matter of certain euganol functionalized silicone polymers useful to make substantive antimicrobial agents. These compounds allow for the topical delivery of euganol to the skin surface, where it has a variety of desirable effects.

17 Claims, No Drawings

SILICONE FUNCTIONALIZED EUGENOL ESTERS

FIELD OF THE INVENTION

This invention relates to composition of matter of certain eugenol functionalized silicone polymers useful to make substantive delivery systems for eugenol to the skin. Eugenol applied to the skin is an effective herbal remedy for a variety of conditions including male pattern baldness.

BACKGROUND AND ART

Clove bud oil has long been used as a herbal remedy. The oil is distilled from the dried-flower buds. It is used in many natural-based toothpastes. It is also a strong insect repellent, and especially useful as a moth repellent. Clove bud oil is a strong antiseptic, anti-spasmodic. Clove bud is also anti viral, anti fungal and healing, and the second most powerful essential oil-directly behind Tea tree oil (melaleuca alternifolia). Clove bud oil has wonderful soothing and calming aromatherapy benefits.

This particular oil comes from the buds of cloves which are known worldwide as a domestic spice. The oil has been used traditionally to remedy skin infections and to reduce digestive upsets. It is also used to kill intestinal parasites and to aid in childbirth. A tea that is made from cloves is often used to relieve nausea. In Chinese history the bud oil has been used for the symptoms above as well as for diarrhea, hernias, bad breath and bronchitis.

The oil can be used to reduce acne, athlete's foot and pain from burns. It has also been found that the oil is a very effective insect repellent and will relieve the pain of most toothaches, ulcers and wounds. The vapors of this oil are found to have beneficial effects on arthritis, rheumatism and most sprains.

The vapor generated from this oil are attributed to eugenol, a volatile material that is very difficult to deliver to the skin as a pure compound. The incorporation of eugenol into a silicone ester having differing amount of polyoxyalkylene groups results in a delivery system for the eugenol that makes delivery of the volatile portion possible.

DESCRIPTION OF THE INVENTION

OBJECTIVE OF THE INVENTION

It is the object of the invention to provide silicone functionalized eugenol esters that provide a mechanism by which eugenol can be delivered over time by hydrolysis of the ester bond linking it to silicone.

SUMMARY OF THE INVENTION

The compounds of the present invention conform to the following structure:

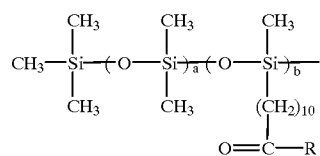

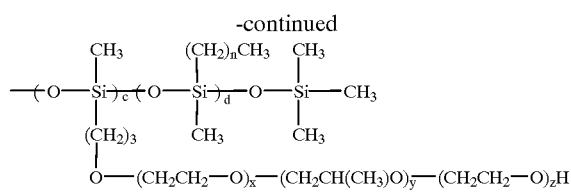

wherein;

a is an integer ranging from 0 to 2000;

b is an integer ranging from 1 to 20;

c is an integer ranging from 1 to 20;

d is an integer ranging from 0 to 20;

n is an integer ranging from 10 to 20;

x is an integer ranging 0 to 20;

y is an integer ranging 0 to 20;

z is an integer ranging 0 to 20;

R is:

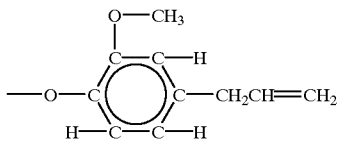

DETAILED DESCRIPTION OF THE INVENTION

The silicone esters of the present invention are made by the reaction of eugenol and certain methyl ester containing silicone compounds.

Eugenol conforms to the following structure:

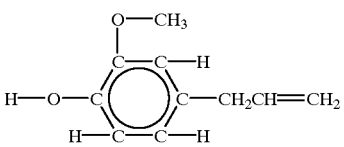

The OH group is reacted with a carboxy methyl ester silicone conforming to the following structure:

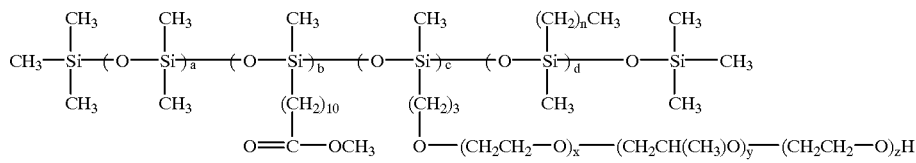

To give the desired compounds:

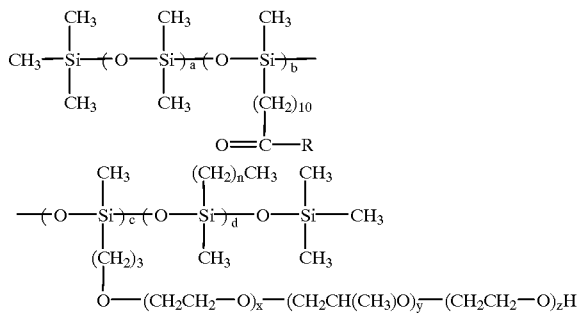

wherein;
a is an integer ranging from 0 to 2000;
b is an integer ranging from 1 to 20;
c is an integer ranging from 1 to 20;
d is an integer ranging from 0 to 20;
n is an integer ranging from 10 to 20;
x is an integer ranging 0 to 20;
y is an integer ranging 0 to 20;
z is an integer ranging 0 to 20;
R is

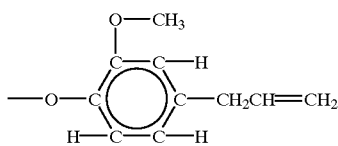

It should be clear that the compounds of the present invention offer the possibility of making delivery products that can be used in many different applications areas. Products can be made with varying solubility in water, silicone compounds, and oil. The different solubilities of the compounds come by changing the values of "a", "c" and "d" in the molecule. By increasing the value of "a" increased silicone solubility is achieved. By increasing the value of "c", increased water solubility is achieved. Alternatively, by increasing the values of "x", "y" and "z" differing water solubility can be achieved. Finally, by increasing the value of "d", the oil solubility will increase. Interestingly, by increasing the value of "b" the amount of active eugenol in the molecule will increase.

The ability to place the compound into any solvent desired allow for the formulation of products for many personal care applications.

The silicone ester derivative of eugenol as contemplated by this invention has improved substantivity to hair, skin and as such is not prone to wash off these substrates. The fact that the compounds of the present invention are esters makes them slowly hydrolyze to release the very eugenol molecule that is the active ingredient.

The amount of silicone eugenol ester necessary to properly effectuate the desired characteristics to the hair and skin ranges from a ratio of wt % between the substrate and the weight of silicone ester should be from about 100:0.01 to about 100:1. Preferably, this range is from about 100:0.03 to about 100:0.6, and most preferably from about 100:0.1 to about 100:0.25.

EXAMPLE

Silicone Methyl Ester

The methyl ester is prepared by the hydrosilylation reaction of a silicone polymer and specific alpha vinyl compounds.

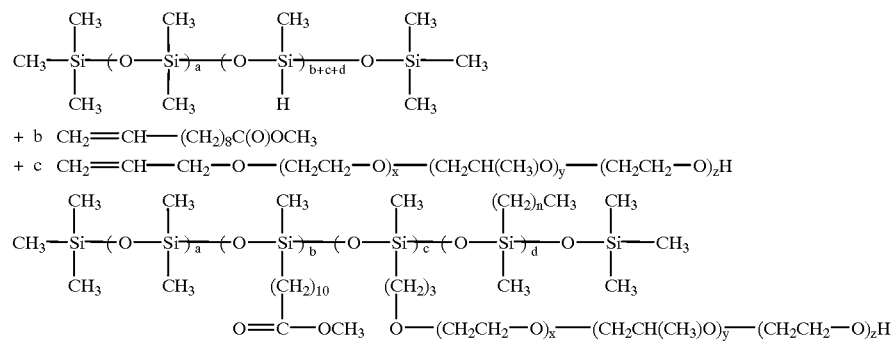

wherein;
 a is an integer ranging from 0 to 2000;
 b is an integer ranging from 1 to 20;
 c is an integer ranging from 1 to 20;
 d is an integer ranging from 0 to 20;
 n is an integer ranging from 10 to 20;
 x is an integer ranging 0 to 20;
 y is an integer ranging 0 to 20;
 z is an integer ranging 0 to 20.

The preparation of the intermediate is critical to the synthesis of the compounds of the present invention. If one tries to hydrosilylate a carboxylic acid directly, the reaction fails. The carboxylic acid group reacts with the Si—H and the desired product is not achieved. The hydrosilylation using the methyl ester however is essentially quantitative and proceeds to give the desired product.

EXAMPLES

Raw Materials

1. Polymer Synthesis

Preparation of Silanic Hydrogen Containing Intermediates

Silicone intermediates of the type used to make the compounds of this invention are well known to those skilled in the art. International Publication (Silicone Alkylene Oxide Copolymers As Foam Control Agents) WO 86/0541 by Paul Austin Sep. 25, 1986) p.16 (examples 1 to 6) teaches how to make the following intermediates, and is incorporated herein by reference.

Hydrosilylation

Hydrogen Containing Compounds (Comb Type)

The polymers used as raw materials are known to those skilled in the art and conform to the following structure:

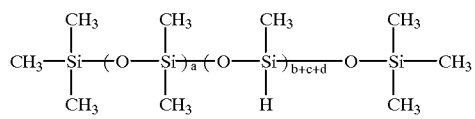

Compounds of this type are available from Siltech Corporation Toronto Ontario Canada.

| Example | Austin Example | a | b | Average Molecular Weight | Equivalent Molecular |
|---|---|---|---|---|---|
| 1 | 1 | 20 | 3 | 1,850 | 551 |
| 2 | 4 | 160 | 5 | 24,158 | 4,831 |
| 3 | 6 | 20 | 10 | 2,258 | 225 |

Compounds of this type are also available commercially from Siltech Corporation Toronto Ontario Canada. The structures were determined using silicone nmr and the chemistries were described using experimentally determined structures. Trade names are given merely for reference.

| Example | Siltech Name | a | b |
|---|---|---|---|
| 4 | Siltech D-116 | 9 | 4 |
| 5 | Siltech H-345 | 22 | 5 |
| 6 | Siltech C-106 | 50 | 10 |

-continued

| Example | Siltech Name | a | b |
|---|---|---|---|
| 7 | Siltech ZZ-302 | 70 | 20 |
| 8 | Siltech XX-456 | 50 | 60 |
| 9 | Siltech J-456 | 10 | 20 |
| 10 | Siltech G-456 | 0 | 60 |

2. Methyl Undecylenate

Example 11

Methyl undecylenate is an item of commerce and conforms to the following structure:

$$CH_2=CH(CH_2)_8-C(O)-OCH_3$$

As previously stated, the reaction requires the reaction of an ester, not the acid directly. The reason for this is that is the reaction is conducted using undecylenic acid the acid group reacts with the Si—H and does not give the desired product. This is a critical unappreciated step in the practice of this technology.

3. Alkoxylated Allyl Alcohols

Alkoxylated allyl alcohol conforms to the following structure:

$$CH_2=CH-CH_2-(CH_2CH_2-O)_x-(CH_2CHCH_3O)_yH$$

wherein x and y are integers independently ranging from 0 to 20.

Compounds of this type are also available commercially from Siltech Corporation Toronto Ontario Canada. The structures were determine using carbon nmr and wet analysis. The chemistries were described using experimentally determined structures. Trade names are given merely for reference.

| Example | x | y |
|---|---|---|
| 12 | 0 | 0 |
| 13 | 8 | 0 |
| 14 | 20 | 20 |
| 15 | 16 | 8 |
| 16 | 5 | 5 |
| 17 | 25 | 25 |
| 18 | 12 | 6 |
| 19 | 9 | 9 |
| 20 | 0 | 9 |

4. Alpha Olefin

Alpha olefins are items of commerce and are available from a variety of sources including Chevron. They conform to the following structure:

$$CH_2=CH-(CH_2)_xCH_3$$

s is an integer ranging from 3 to 50.

| Example | s |
|---|---|
| 21 | 8 |
| 22 | 10 |
| 23 | 12 |
| 24 | 14 |
| 25 | 18 |

5. Hydrosilylation

The hydrosilylation reaction used to make the compounds of this invention is well known to those skilled in the art. One of many references is International Publication (Silicone Alkylene Oxide Copolymers As Foam Control Agents) WO 86/0541 by Paul Austin (Sep. 25, 1986) p.19.

General Reaction Process (Hydrosilylation)

To a suitable flask fitted with a mechanical agitator, thermometer with a Therm-o-watch temperature regulator, nitrogen sparge tube vented reflux condenser and heating mantle is added the specified quantity of methyl undecylenate (example 11), allyl alcohol alkoxylates (examples 12–20), and alpha olefin (examples 21–25) examples. Next is added the specified number of grams of the specified hydrosilylation intermediate (Example # 1–10) and isopropanol. The temperature is increased to 85° C. and 3.5 ml of 3% $H_2PtCl_6$ in ethanol is added. An exotherm is noted to about 95° C., while the contents are stirred for about 2 hours. During this time silanic hydrogen concentration drops to nil. Cool to 65° C. and slowly add 60 g of sodium bicarbonate. Allow to mix overnight and filter through a 4-micron pad. Distill off any solvent at 100° C. and 1 torr.

Example 26

To a suitable flask fitted with a mechanical agitator, thermometer with a Therm-o-watch temperature regulator, nitrogen sparge tube vented reflux condenser and heating mantle is added 200.0 grams of methyl undecylenate (example 11), 915.4 grams of allyl alcohol alkoxylate (example 16), 1687.7 grams of hydrosilylation intermediate (Example # 15) and 750 grams of isopropanol.

Heat to 85° C. and add 3.5 ml of 3% $H_2PtCl_6$ in ethanol. An exotherm is noted to about 95° C., while the contents are stirred for about 2 hours. During this time silanic hydrogen concentration drops to nil. Cool to 65° C. and slowly add 60 g of sodium bicarbonate. Allow to mix overnight and filter through a 4-micron pad. Distill off any solvent at 100° C. and 1 torr.

Examples 26–55

| | Silanic Polymer | | Allyl Alkoxylate | | Alpha Olefin | |
|---|---|---|---|---|---|---|
| Example | Example | Grams | Example 11 Grams | Example | Grams | Example | Grams |
| 26 | 1 | 2600.8 | 281.0 | 12 | 165.2 | 21 | 0 |
| 27 | 2 | 2617.0 | 42.0 | 13 | 348.1 | 21 | 0 |
| 28 | 3 | 497.1 | 218.0 | 14 | 2321.2 | 21 | 0 |
| 29 | 4 | 703.4 | 129.5 | 15 | 2188.6 | 21 | 0 |
| 30 | 5 | 1522.5 | 286.4 | 16 | 1238.7 | 21 | 0 |
| 31 | 6 | 522.7 | 46.1 | 17 | 2438.9 | 21 | 0 |
| 32 | 7 | 423.0 | 63.6 | 18 | 2524.0 | 21 | 0 |
| 33 | 8 | 387.3 | 102.1 | 19 | 2527.6 | 21 | 0 |
| 34 | 9 | 543.5 | 254.2 | 20 | 2244.7 | 21 | 0 |
| 35 | 10 | 1360.6 | 710.0 | 12 | 1046.6 | 21 | 0 |
| 36 | 1 | 2064.2 | 222.7 | 13 | 463.5 | 21 | 286.6 |
| 37 | 2 | 1942.5 | 31.1 | 14 | 991.7 | 22 | 39.9 |
| 38 | 3 | 691.9 | 121.3 | 15 | 2050.9 | 23 | 156.1 |
| 39 | 4 | 1223.6 | 225.2 | 16 | 1298.7 | 24 | 289.8 |
| 40 | 5 | 607.9 | 57.2 | 17 | 2270.9 | 25 | 73.6 |
| 41 | 6 | 1229.4 | 108.4 | 18 | 1540.8 | 21 | 139.4 |
| 42 | 7 | 886.1 | 80.0 | 19 | 1978.8 | 22 | 68.5 |
| 43 | 8 | 581.7 | 77.0 | 20 | 2255.8 | 23 | 98.6 |
| 44 | 9 | 1589.3 | 445.5 | 12 | 656.4 | 24 | 382.5 |
| 45 | 10 | 429.1 | 112.1 | 13 | 2333.2 | 25 | 144.3 |
| 46 | 1 | 1261.7 | 136.2 | 14 | 1449.7 | 21 | 175.2 |
| 47 | 2 | 2430.1 | 39.0 | 15 | 437.6 | 22 | 99.9 |
| 48 | 3 | 1038.5 | 182.2 | 16 | 1575.3 | 23 | 234.4 |
| 49 | 4 | 478.9 | 88.2 | 17 | 2334.1 | 24 | 113.4 |
| 50 | 5 | 1182.4 | 111.2 | 18 | 1581.8 | 25 | 143.1 |
| 51 | 6 | 1201.7 | 105.0 | 19 | 1573.8 | 21 | 136.3 |
| 52 | 7 | 1209.9 | 109.8 | 20 | 1605.6 | 22 | 93.6 |
| 53 | 8 | 1799.5 | 237.1 | 12 | 697.9 | 23 | 305.0 |
| 54 | 9 | 665.1 | 124.4 | 13 | 2071.2 | 24 | 160.1 |
| 55 | 10 | 123.1 | 64.3 | 14 | 2740.5 | 25 | 82.8 |
| 56 | 4 | 1066.0 | 197.0 | 13 | 1228.0 | 21 | 0 |
| 57 | 4 | 534.0 | 197.0 | 13 | 409.0 | 21 | 0 |
| 58 | 4 | 355.0 | 197.0 | 13 | 136.0 | 21 | 0 |

Eugenol Reaction Examples 59–75

The compounds made in examples 26–58 are methyl esters as prepared. They are reacted with eugenol to produce the compounds of the present invention.

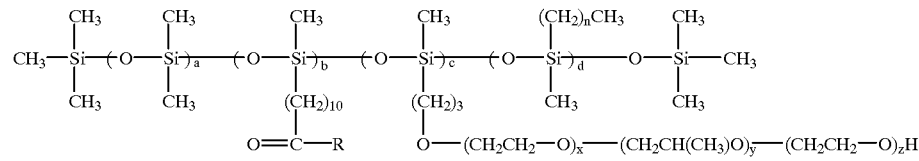

R is;

[structure: eugenol group with O—CH$_3$, —O—, H, and —CH$_2$CH=CH$_2$ substituents on benzene ring]

Example 59–75

In a suitable reaction flask equipped with a thermometer, heating mantle, and a condenser to remove methanol is added the specified amount of the specified silicone methyl ester is added 180.0 grams of the eugenol. The reaction mass is heated to 190° C. to 200° C. The reaction begins at about 170° C. Allow the methanol to distill off as the reaction proceeds. After the reaction progress is followed by hydroxyl value which meets theoretical within 12 hours.

|         | Methyl Ester |        |
| ------- | ------------ | ------ |
| Example | Example      | Grams  |
| 59      | 26           | 3047.0 |
| 60      | 27           | 3007.1 |
| 61      | 28           | 947.2  |
| 62      | 29           | 3021.5 |
| 63      | 30           | 3047.6 |
| 64      | 31           | 3007.7 |
| 65      | 32           | 3028.6 |
| 66      | 33           | 3016.4 |
| 67      | 34           | 3042.4 |
| 68      | 35           | 3117.2 |
| 69      | 36           | 3038.0 |
| 70      | 37           | 3005.3 |
| 71      | 38           | 3020.1 |
| 72      | 39           | 3037.6 |
| 73      | 40           | 3008.1 |
| 74      | 41           | 3017.8 |
| 75      | 42           | 3013.1 |

What is claimed:

1. A silicone polymer conforming to the following structure:

[silicone polymer structure with Si—O repeating units, subscripts a, b, c, d, (CH$_2$)$_{10}$, O=C—R, (CH$_2$)$_n$CH$_3$, (CH$_2$)$_3$, and terminal O—(CH$_2$CH$_2$—O)$_x$—(CH$_2$CH(CH$_3$)O)$_y$—(CH$_2$CH$_2$—O)$_z$H]

wherein;
   a is an integer ranging from 0 to 2000;
   b is an integer ranging from 1 to 20;
   c is an integer ranging from 1 to 20;
   d is an integer ranging from 0 to 20;
   n is an integer ranging from 10 to 20;
   x is an integer ranging 0 to 20;
   y is an integer ranging 0 to 20;
   z is an integer ranging 0 to 20;
   R is

[eugenol group structure]

2. A silicone polymer of claim 1 wherein d is an integer ranging from 0.
3. A silicone polymer of claim 1 wherein d in an integer ranging from 1 to 5.
4. A silicone polymer of claim 1 wherein b is an integer ranging from 6 to 20.
5. A silicone polymer of claim 1 wherein c is an integer ranging from 1 to 5.
6. A silicone polymer of claim 1 wherein c in an integer ranging from 6 to 20.
7. A silicone polymer of claim 1 wherein a is an integer ranging from 1 to 5.
8. A silicone polymer of claim 1 wherein a in an integer ranging from 6 to 20.
9. A process for treating skin, which comprises contacting the skin with an effective treatment concentration of a silicone polymer conforming to the following structure:

[silicone polymer structure same as claim 1]

wherein;
   a is an integer ranging from 0 to 2000;
   b is an integer ranging from 1 to 20;
   c is an integer ranging from 1 to 20;
   d is an integer ranging from 0 to 20;
   n is an integer ranging from 10 to 20;
   x is an integer ranging 0 to 20;
   y is an integer ranging 0 to 20;
   z is an integer ranging 0 to 20;
   R is;

[eugenol group structure]

10. A process of claim 1 wherein the effective treatment concentration ranged from 0.001 to 20% by weight of the silicone polymer.
11. A process of claim 9 wherein d is an integer ranging from 0.
12. A process of claim 9 wherein d in an integer ranging from 1 to 5.

13. A process of claim 9 wherein b is an integer ranging from 6 to 20.

14. A process of claim 9 wherein c is an integer ranging from 1 to 5.

15. A process of claim 9 wherein c in an integer ranging from 6 to 20.

16. A process of claim 9 wherein a is an integer ranging from 1 to 5.

17. A process of claim 9 wherein a in an integer ranging from 6 to 20.

* * * * *